(12) United States Patent  
Carlucci et al.

(10) Patent No.: US 12,130,190 B2  
(45) Date of Patent: Oct. 29, 2024

(54) LOAD SENSING DEVICE FOR ARTICLES OF FOOTWEAR

(71) Applicant: ECCO Sko A/S, Bredebro (DK)

(72) Inventors: Patrizio Carlucci, Bredebro (DK); Panagiotis Mytaros, Bredebro (DK)

(73) Assignee: ECCO Sko A/S, Bredebro (DK)

( * ) Notice: Subject to any disclaimer, the term of this patent is extended or adjusted under 35 U.S.C. 154(b) by 505 days.

(21) Appl. No.: 17/425,552

(22) PCT Filed: Jan. 24, 2020

(86) PCT No.: PCT/EP2020/051697  
§ 371 (c)(1),  
(2) Date: Jul. 23, 2021

(87) PCT Pub. No.: WO2020/152305  
PCT Pub. Date: Jul. 30, 2020

(65) Prior Publication Data  
US 2022/0334009 A1    Oct. 20, 2022

(30) Foreign Application Priority Data

Jan. 24, 2019 (EP) .................................... 19153496

(51) Int. Cl.  
*G01L 1/22* (2006.01)  
*A43B 3/44* (2022.01)  
(Continued)

(52) U.S. Cl.  
CPC .............. *G01L 1/2206* (2013.01); *A43B 3/44* (2022.01); *A61B 5/1036* (2013.01); *A61B 5/6807* (2013.01)

(58) Field of Classification Search  
CPC ........... G01L 1/2206; A43B 3/44; A43B 3/34; A61B 5/1036; A61B 5/6807; A61B 2562/0219; A61B 2562/0252  
See application file for complete search history.

(56) References Cited

U.S. PATENT DOCUMENTS 5,325,869 A    7/1994   Stokes  
6,174,294 B1 *  1/2001   Crabb ................. A61B 5/1036  
                                            600/595

(Continued)

FOREIGN PATENT DOCUMENTS

CN    104244756    12/2014  
CN    205250477     5/2016

(Continued)

OTHER PUBLICATIONS

Extended EP Search Report for corresponding EP Patent Application No. 19153496.5 dated Jul. 1, 2019, 8 pages.

(Continued)

*Primary Examiner* — Francis C Gray  
(74) *Attorney, Agent, or Firm* — Lee & Hayes, P.C.

(57) ABSTRACT

A load sensing device for a shoe includes a base element having a first side and an opposite second side. The first side has a predefined area. A first load sensing element and a second load sensing element are positioned at the first side of the base element. The first load sensing element is positioned in a first area of the predefined area of the first side, and the second load sensing element is positioned in a second area of the predefined area of the first side. The first load sensing element has a fixed position relative to the second load sensing element during use. The first load sensing element and the second load sensing element are configured to measure a load applied to at least part of the predefined area of the first side.

15 Claims, 2 Drawing Sheets

(51) Int. Cl.
*A61B 5/00* (2006.01)
*A61B 5/103* (2006.01)

(56) References Cited

U.S. PATENT DOCUMENTS

| | | | | |
|---|---|---|---|---|
| 2011/0199393 | A1* | 8/2011 | Nurse | G06F 3/017 |
| | | | | 345/665 |
| 2015/0359457 | A1 | 12/2015 | Blumenthal et al. | |
| 2017/0115171 | A1* | 4/2017 | Huang | A61B 5/6807 |
| 2017/0336273 | A1* | 11/2017 | Elangovan | A43B 17/18 |
| 2018/0094991 | A1 | 4/2018 | McMillen et al. | |
| 2019/0175107 | A1* | 6/2019 | Lu | A61B 5/0022 |

FOREIGN PATENT DOCUMENTS

| | | |
|---|---|---|
| CN | 105795571 | 7/2016 |
| CN | 105979869 | 9/2016 |
| CN | 206079229 | 4/2017 |
| CN | 107003188 | 8/2017 |
| CN | 108135314 | 6/2018 |
| CN | 109106342 | 1/2019 |
| CN | 109152445 | 1/2019 |
| JP | 2004239622 | 8/2004 |
| KR | 20170123120 | 11/2017 |
| TW | 201315400 | 4/2013 |
| WO | WO 2017085218 | 5/2017 |

OTHER PUBLICATIONS

PCT Search Report for corresponding PCT Application No. PCT/EP2020/051697 dated Mar. 23, 2020, 4 pages.
China Search Report for corresponding Chinese Patent Application No. 2020800098573 dated Nov. 24, 2022, 2 pages.
Chinese Office Action for corresponding Chinese Patent Application No. 202080009857.3 dated Sep. 24, 2023, 5 pages.

* cited by examiner

LOAD SENSING DEVICE FOR ARTICLES OF FOOTWEAR

This Application claims priority to PCT/EP2020/051697, filed Jan. 24, 2020, which claims priority to EP 19153496.5, filed Jan. 24, 2019, the entireties of which are incorporated herein by reference.

TECHNICAL FIELD

The present description relates to an improved load sensing device for a footwear.

BACKGROUND

Comfort of shoes is important to the persons wearing them, both in respect of the general well-being of the wearer, as shoes are often worn every day and for many hours, but also in connection with the performance of the wearer when using the shoes when performing sport activities such as running or golf.

A number of different devices exists that can be connected to the shoe and thereby used for measuring different motion parameters while wearing the shoe, e.g. such as a device mounted on a running shoe for measuring the speed and motion of the runner wearing the shoe with the device. Typically, such devices are attached to the shoe as a separate unit.

Further, when it comes to determining the comfort of a shoe, a number of parameters can be detected and one parameter that is useful, is how the foot engages the sole of the shoe during walking, running or other activities.

There exist systems where pressure sensors are positioned in the sole for measuring the pressure. Typically, in these solutions, pressure sensors are added as a separate sole unit, where transducers are positioned in different areas relative to the sole and then connected to an electronic circuit for processing the output from the sensors to a central unit in the shoe pad.

U.S. Pat. No. 9,763,489 discloses a sensor system which is adapted for use with an article of footwear and includes an insert member including a first layer and a second layer, a port connected to the insert and configured for communication with an electronic module, a plurality of force and/or pressure sensors on the insert member, and a plurality of leads connecting the sensors to the port. The plurality of pressure sensors are positioned on a flexible layer, where the flexible layer is adapted to follow the contour of the shoe during use, which means that the force and/or pressure sensors move relative to each other during use. Furthermore, the pressure sensors are positioned in different parts of the shoe so that there is little or no correlation between the sensors other than identifying a load on a specific part of the foot.

A problem with the pressure sensor systems known from the prior art is that they are complicated systems comprising wirings running along the length and breadth of the sole to connect parts placed at various locations on the sole. During use, the sole is exposed to shear and compressive and tractive forces because of movement of the user, these forces exerting considerable wear on a typical shoe. A shoe is most often considered worn out when the physical appearance has dropped below some threshold dependent on the preferences of the user, where solid materials such as rubber, leather or robust thread has given way to the wear. Copper wirings running the length and/or breadth of the sole are exposed to bending, shearing, compression, traction and humidity, and typically degrades and/or breaks before the shoe or sole is otherwise considered worn out, whereby the user loses a key functionality of his/her purchase, namely the sensor, or s/he will have to buy new shoes or soles, wasting the otherwise functional materials of the shoe or sole. When mounting an element in a shoe for a projected prolonged period of wear, the device benefits considerably from being built in a robust, durable and stable manner; this allows it to better withstand the considerably extreme forces a shoe sole is subjected to during use. Additionally, existing systems rely on additional transducers between the pressure sensors and the wireless transmitting unit.

GENERAL DESCRIPTION

In accordance with the present description, there is provided a load sensing device for a shoe comprising: a base element having a first side and an opposite second side, where the first side has a predefined base area, a first load sensing element and a second load sensing element positioned at the first side of the base element, wherein the first load sensing element is positioned in a first area of the predefined area of the first side and the second load sensing element is positioned in a second area of the predefined area of the first side, wherein the first load sensing element is has a fixed position relative to the second load sensing element during use, where the first load sensing element and the second load sensing element are configured to measure a load applied to at least part of the predefined area of the first side.

This means that the load sensing device may measure loads from two positions on the base area, where each of the two positions represent the load being applied to the same predefined base area at different times. Thus, this means that the load being applied, which may be seen as a load that is applied to the load sensing device using the sole of the foot (the bottom of the foot), is measured by separate load sensing devices which means that the measurement may be seen as being shifted in phase. One example of this may be seen as when a person walks or runs, only a part of the sole of the foot contacts the ground, and during the movement the sole is rotated so that more and more of the sole contacts the ground, until the movement is inversed so that less and less of the sole contacts the ground up to the point where the sole releases the ground. By providing a base element, which may be arranged inside the sole of a shoe, where the base element has a base area having at least two load sensing elements, the load sensing elements will measure different parts of the contact of the sole to the load sensing device during a walking movement, running movement, or even measure the loads in different positions when the person stands in a still position.

Fixed position may mean a fixed position in three dimensions, so that the first and the second load sensing elements do not move relative to each other. This means that when a load is applied to both the first load sensing element and the second load sensing element, the two load sensing elements are measuring corresponding loads. The load sensing elements may have an axis of measurement, which means that when the load is measured in the first and/or the second load sensing elements the measurement axis are stationary relative to each other, in all directions.

The load sensing device may be positioned inside the sole of a shoe, so that when a load is measured, the sole of the shoe may be positioned between the surface contacted by the shoe and a second side (ground facing side) of the load sensing device.

The term "fix" and "fixed" may be understood as meaning to make something fast, firm, stable, rigid or permanent positioning, and should be understood as not be changing over time or use.

The load sensing elements may be positioned in an article of footwear, where the orientation of the load sensing elements during use, i.e. during a measurement, will not change. Thus, even if the sole of the article of footwear is bent, compressed, expanded, twisted or in any way manipulated, the position of the first load sensing element will remain the same relative to the second load sensing element. The position may be seen as not only the two-dimensional position inside the shoe, where the first dimension (x) may be the width and the second dimension (x) may be seen as the length, but also in a third dimension which is the height. Sensors that are e.g. positioned on a flexible sheet, or are positioned discretely in the sole of the shoe will not maintain their position relative to each other, as any movement in any part of the shoe will change the positioning of one sensor relative to a second sensor. An example may e.g. be seen when a first sensor is positioned on a medial side of the footwear, and a second sensor is positioned on a lateral side of the footwear, any application of force to one of the sensors will move one of the sensors relative to each other. The present disclosure provides a solution where a movement of one sensor (load sensing element) will result in a corresponding movement of a second sensor, so that the positioning of the sensors is maintained relative to each other. This may be obtained by using a base plate that is capable of transmitting movement from one sensor to the other. Within the understanding of the present invention, the position of the first and the second sensor may change position relative to the sole assembly of the shoe.

Thus the load sensing device is measuring a load to the same predefined area in two different positions, which means that it may be measured which load sensing element is measuring the first application of contact between the outsole of the foot and the load sensing device, e.g. during gait, and where the second load sensing element may be not measure anything, it is possible to see the direction of load during the gait, as the user will know the physical position of the load sensing elements during use. Thus, it is possible to infer by the phase shifting of the measurement which direction the load is applied on the foot.

In one example, the first and second load sensing element may be positioned side by side where one load sensing element is positioned on a medial side and the second load sensing element is positioned on a lateral side of the sole of the shoe, it may be possible to identify whether a user has an initial strike on the lateral side of the foot, on the medial side of the foot, or where the user has an initial strike that is neutral, where both load sensing elements are activated at substantially the same time. Thus, it may possible to identify whether the user has a neutral position, has a pronated position or has a supinated position of the foot during his natural gait (dynamic positioning) or in his foot posture during standing position (static positioning). The terms neutral position, pronated position or a supinated position should be understood within the understanding of gait analysis known in the art, where the positioning of the foot of the user is defined in relation to the lower leg of the user during dynamic or static movement.

In other examples the positioning of the load sensing elements may be different, where the two load sensing elements may be aligned at a diagonal, where one load sensing element is positioned in a medial position, and the second load sensing element is at a lateral position, but where the two load sensing elements are positioned at different longitudinal positions along the length of the sole. Alternatively, the two load sensing elements may be positioned in the same transverse area (medial area, central area, lateral area) but at two different longitudinal positions.

The base element may e.g. be a plate having a predefined surface area on its first side, where the base element may be adapted to hold one or more load sensing elements on one of its sides, where the base element may be used to fix the position of the load sensing elements in relation to each other. The base element may be adapted to fix the positions of the load sensing elements in both longitudinal and transverse directions, as well as in a direction that is normal to the longitudinal and transverse directions.

The load sensing element may be any kind of element that is capable of transforming a physical force into an electrical signal, where the form of the electrical signal is representative of the physical force that is applied to the load sensing element. The magnitude of the electrical signal may be directly proportional to the force being measured.

The load sensing device may be a load measuring device, where the device is capable of registering and measuring loads and interfacing with a memory The predefined base area may have a size that is capable of holding at least two load sensing elements. Thus, the predefined base area may have a size that is larger than the size of the areas that hold the load sensing element. The predefined base area may e.g. have a size that is at least twice the size of the first area or the second area. The size of the predefined base area may be even larger when the area has a plurality of load sensors, where the minimum size of the predefined base area may e.g. be the total area of the load sensing elements that are to be positioned on the base plate. The predefined base area may be a predefined base surface area, where the predefined base area may be a surface area on the base element.

The surface area of the first area and/or second area of the base element may have a size that is substantially equal to the size of the load sensing element in two dimensions. Thus, the size of the surface area of the base element may be e.g. at least twice the size of the surface area size of the load sensing element.

The first and/or the second load sensing element may be positioned in such a way that when a force is applied on the first side of the base element, the load sensing element is configured to register and/or measure the load being applied. This means that the load sensing element may be positioned on top of the base element, as layer that is positioned between the base element and the foot. Optionally, the load sensing element may be embedded in the base element. Within the meaning of the present disclosure, the application of layers between the base element and the load sensing element, or the application of layers on top of the load sensing element are to be understood as part of the invention, as the requirement of the load sensing element is that the load sensing element should be capable of measuring a force that is applied to the base element in a direct or indirect manner.

By providing a load sensing device in the shoe, where the load sensing device may measure the gait of the user, the standing of the user or any movement of the user that may be translated to from the outsole of the foot and towards the ground, it is possible to provide measurements for a user in a natural environment, i.e. during street running, playing golf, walking, instead of confining such measurements to a measurement location, such as often is the case where a running or walking analysis is made using pressure plates in the ground, cameras, etc. at a measurement location. Thus, the user may wear the load sensing device during natural activities where the user may forget that the measurements are being made and will therefore use his/her natural motion and not be self-conscious when the measurements are being made.

The first area and the second area may be separated from each other. The areas for the load sensing elements are separated from each other, so that the loads that are measured which are applied to the first area are measured from separate positions on the first area. Thus, the first load sensing element may be separated from the second load sensing element. The first and the second load sensing elements, and subsequent load sensing elements, if present, may be applied in the form of a load sensing array, where each load sensing element is adapted to measure a predefined first area which is different from the second area, and any subsequent areas. Within the understanding of the present invention the separation of the load sensing elements is not necessarily a physical separation of individual components (load sensing elements) is to be understood as a separation of the measurement area of the load sensing elements.

The load sensing element may be an active or a passive load sensing element. An active load sensing element is known in the art and has an electrical input and where the change in force represents a change in the electrical input that is corresponding to the load being applied, e.g. a resistor such as a strain gauge load sensing element. A passive load sensing element may e.g. be a piezoelectric load sensor element, where the force applied to the load sensing element generates a voltage output, e.g. a piezoelectric load sensing element.

In one exemplary embodiment, the load sensing device may comprise a plurality of load sensing elements, where each load sensing element is spaced away from another load sensing element.

In one exemplary embodiment the load sensing device may be a load sensing device for measuring loads during human gait. The load sensing device may be positioned between the foot of the user and the ground. The load sensing device may be positioned in an article of footwear, so that the positioning of the load sensing may be fixed relative to the foot of the wearer.

In one exemplary embodiment the first load sensing element may be configured to measure a load applied to a first region of the heel of the user, where the second load sensing element may be configured to measure a load applied to a second region of the heel of the user, where the first region of the heel is different from the second region of the heel. A third load sensing element may be configured to measure a load applied to a third region of the heel of the user. A subsequent load sensing element may be adapted to measure a load applied to a subsequent region of the heel of the user, where the subsequent region may be different from the first, second and/or third regions of the heel. In accordance with the present invention, the heel of the user may be understood as the heel region of the sole of the foot.

In one embodiment the first and/or the second load sensing element may be configured to measuring a plurality of values of loads. Thus, this means that the load sensing element may be capable of registering more than one value of the load to be measured, where the value of the load may be measured in more than one bit (two values), which is only capable of measuring whether a load exceeds a certain threshold. The load sensing element may produce a continuous electrical signal which is time varying. The load sensing element may further provide an analogue or a digital signal, or may provide an analogue signal that may be converted to a digital signal. The plurality of values of loads may be 4 bits, 8 bits, 16 bits, 32 bits or any suitable plurality of loads that may be envisioned by the user of the load sensing device.

In one embodiment the predefined area of the first side may be configured to be positioned in the heel area of the shoe. This means that the predefined area does not stretch from the heel area to another area, as this would prevent natural movement.

In one embodiment the first area of the predefined area of the first side may be separated from the second area of the first side. The separation may ensure that the In one embodiment the base area may be less than 80 $cm^2$, where the base area may be less than 50 $cm^2$, where the base area may be less than 45 $cm^2$, where the base area may be less than 40 $cm^2$, where the base area may be less than 30 $cm^2$, where the base area may be less than 25 $cm^2$. A midsole or an outsole of a shoe having the size 42 (European size) may at least have an area that is more than 130 $cm^2$, where it is advantageous that the size of the base area is at least less than half the size of the sole of the shoe. The size of the base area may be even smaller than this, where the size may be less than ¼ of the size of the sole of the shoe. One advantage of the size of the base area may be seen where the base area may be implemented into a shoe in a certain area of the shoe, i.e. the heel or the forefoot, where the load sensing device may measure a limited area of the outsole of the foot and not many parts of the foot. Within the context of the present application the parts of the foot may be defined as the heel area, the arch area and/or the forefoot area. Thus, the base area may be positioned in the heel area of the sole without stretching into the arch and/or forefoot area, or that the base area may be positioned in the arch area of the sole without stretching into the heel and/or the forefoot area, or that the base area may be position in the forefoot area without stretching into the heel and/or the arch area.

In one embodiment the load sensing device and/or the base element may comprise electrical connections providing electrical communication from the first and the second load sensing elements to electrical components. This means that the base element may have integrated electrical connections, which allow the transmission of electrical signal from one component to another component. This may as an example be where the base element may be constructed as an integrated circuit board.

In one embodiment wherein the load sensing device may be provided with a housing having at least a first side which covers the first side of the base element and/or the first and/or the second load sensing elements, and wherein first side of the housing may be optionally be flexible allowing force applied to the surface of the housing to be transmitted to the first and/or the second load sensing element. Optionally the first side of the housing may be configured to transmit force from the first side of the housing and to the load sensing element in a direct or indirect manner. A direct manner is where the first side of the housing contacts the load sensing element directly, while an indirect manner may mean that an intermediate element may be positioned between the first side of the housing and the load sensing element.

In one embodiment the housing may comprise a second side which covers the second side of the base element. The second side may optionally be configured to provide a counterforce to the load sensing elements during use. The second side may be constructed to support the base element, that any force that may be applied to the base element is transferred in a mechanical manner to the second side, where the second side may be adapted to be in contact with The housing may provide a waterproof and/or hermetically sealed volume where the load sensing device and/or any electrical components, power source, electrical connectors may be housed, where the housing provides an outer shell for the load sensing device to protect the load sensing device from moisture, dust, shock or any environmental influence that can damage the parts of the load sensing device.

In one embodiment the load sensing element may be a force sensitive resistor, alternatively a piezoelectric sensor. A Force sensitive resistor can be defined as a special type of resistor whose resistance can be varied by varying the force or pressure applied to it. The FSR sensors may be made of a conductive polymer which has a property of changing its resistance based on the force applied to its surface. The force sensitive resistor may have a thickness that is less than 2 mm. The force sensitive resistor may be a layered construction having a plurality of layers, where one of the layers of the force sensitive resistor may be at least part of the base element.

In one embodiment the load sensing element may have a first surface configured to receive an external load and/or a second opposing surface which may be mounted on a rigid surface, where the rigid surface provides a counterforce to the load which the load sensing element is configured to measure. The rigid surface may be part of the base element. The rigid surface may comprise the first and/or the second load sensing element, where the rigid surface may maintain the position of the first load sensing element and the second load sensing element during use, so that when a load is applied to one or more of the load sensing elements, the rigid surface provides a counterforce to the load.

In one embodiment the base element may be a rigid element. The rigid element may be a plate or an element having a predefined shape, e.g. a planar shape, where the rigidity of the element and the attachment of the load sensing element to the rigid element may ensure that a load sensing element does not move relative to the rigid element and/or another load sensing element. The rigid element may be layered construction, where one layer may hold the first side of the base element, while a second layer may be utilized to provide a rigidity to the first layer. I.e. that one layer provides a rigid support to another layer. Alternatively, the rigid element may be a single layer, where the load sensing element may be attached to one side of the rigid element.

Within the context of the present disclosure the term "rigid" should be understood as a level of stiffness that maintains its shape during use. The use may be seen as when the load sensing device is positioned in a shoe, the rigid surface and/or rigid element maintains it shape when a load is applied to the load sensing device. In other words, the rigidness should be seen as a relative rigidness, where the rigidness ensures that the base element does not bend along with the shoe during use.

In one embodiment the base element may be a printed circuit board, having electrical connections providing electrical communication from the load sensors on the first side of the base element to the second side of the base element. The printed circuit board may ensure that electrical components that are positioned on one side of the circuit board may be electrically connected to optional components that may be posited on the opposite side (second side of the base element). This means that the load sensing elements may be positioned on one side of the base element while any optional electrical components may be provided on the opposite side of the base element, this means that the electrical components may be protected from the load applied to the load sensing device, as the load is configured to be applied to a side of the base element that is void of electrical components other than the load sensing elements. Thus, this means that the electrical components, may be physically isolated from the loads.

In one embodiment the electrical components may be arranged on the opposite second side. The components may be soldered to the second side of the base element, where the electrical connections that connect the load sensing elements to the electrical components may extend from the first side of the base element to the second side of the base element through the base element.

In one embodiment the load sensing device may comprise one or more of a controller, a memory, a NFC device, power source, wireless charging device, wired and/or wireless communication device.

In one embodiment the position of the first load sensing element may be fixed relative to the position of the second load sensing element.

In one embodiment the first side comprises a third load sensing element and/or a fourth load sensing element, and/or a subsequent load sensing element. By providing a subsequent load sensing element to the first side, in addition to the first and the second load sensing elements, the load sensing measurements may rely on further input to analyse the gait of a user. The positioning of the subsequent load sensing elements may be in any direction, where an additional load sensing element that is positioned in front of or behind (in the longitudinal direction) the first and/or the second load sensing elements may add a further measuring element to the longitudinal movement of the foot during a foot-strike. The provision of an additional load sensing element to the side of the first and/or the second load sensing elements (in a transverse direction) the load sensing elements may e.g. add a further measurement to the tilting movement of the foot during a foot-strike. The inclusion of one additional load sensing element in front of or behind the first and/or the second load sensing element does not preclude an additional load sensing element to the side of the first and/or the second load sensing element.

In one embodiment the load sensing device comprises one or more secondary measuring elements for measuring one or more of the following: acceleration, direction, humidity, position, orientation, temperature, barometric pressure and/or angular velocity. The secondary measuring elements may be one or more of the following accelerometer, gyroscope, magnetometer and quaternion. The one or more secondary measuring elements may be positioned on the second side of the base element.

In one embodiment the load sensing device may be provided with a communication interface with a peripheral device, such as a mobile device or a computer, where an operator can monitor the measurements of the load sensing device in real time, and where the measurements may possibly be represented on a visual display for the operator.

In one embodiment the load sensing device may be provided with a power source and a processor as well as a user feedback device. The user feedback device may e.g. be one or more of a visual feedback device, auditory feedback device, a haptic feedback device, or other known feedback devices, where the user feedback device may alert the user of conditions that may be detected by the load sensing device. Such conditions may be user defined and/or generic conditions such as instability, loss of traction, specific types of movements, or other conditions that may occur during dynamic or static movement of the foot of the user. The user feedback device may e.g. be utilized for training the user on a specific movement during dynamic or static motion, where the feedback device may inform the user whether an unwanted movement has been detected, or to notify the user that a desirable movement has been detected. The feedback device may be adapted to work in cooperation with a mobile device, a computer or any kind of peripheral device, or could be adapted to provide the user with direct feedback coming from the load sensing device.

The present disclosure also relates to a method of obtaining load measurements in an article of footwear, the load measurement originating from a sole of a foot of a user comprising: positioning a first load sensing element in a first region of an article of footwear, the first load sensing element providing a first electrical signal, positioning a second load sensing element in a second region of an article of footwear. the second load sensing element providing a second electrical signal, fixing the position of the first load sensing element relative to the second load sensing element during use, and receiving the first and the second electrical signal by a processing unit during use of the article of footwear.

The method may utilize the load sensing device disclosed in the present disclosure to obtain the measurement. The fixation of the first sensor relative to the second sensor may be obtained by positioning the first sensor and the second sensor on a base plate, which is configured to maintain the position of the sensors during use.

The use of the load sensing device may be understood as a situation where the load sensing elements are positioned inside an article of footwear, and where the load sensing elements are used to collect information about the load applied to the load sensing elements while the user is using the article of footwear, during gait, running, playing golf, standing in position, where the signals may be collected for further analysis. The fixation of the first load sensing element relative to any other load sensing element (second, third, fourth, etc) means that it may be possible to mechanically remove artefacts from the signals, such as the softness of a footwear sole assembly, the bending of a footwear sole assembly and difference thickness of a shoe sole assembly.

Furthermore, the fixing of the load cell relative to each other means that load sensing device is measuring the load transmitted from the sole of a user in a same direction at the same time. Thus, a difference in the signals received from a first load sensing element relative to a second load sensing element may represent a movement of the sole of the foot from one position to the other, such as happens during a pronating gait or similar movements where there is a transmittal of load between a surface area and the foot, via the article of footwear.

The disclosure may also relate to a method may also be a method of operating a load sensing device in accordance with the disclosure and/or the claims.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

BRIEF DESCRIPTION OF THE DRAWINGS

The following is an explanation of exemplary embodiments with reference to the drawings, in which.

DETAILED DESCRIPTION

The use of the terms "first", "second", "third" and "fourth", "primary", "secondary", "tertiary" etc. does not imply any particular order, but are included to identify individual elements. Moreover, the use of the terms "first", "second", "third" and "fourth", "primary", "secondary", "tertiary" etc. does not denote any order or importance, but rather the terms "first", "second", "third" and "fourth", "primary", "secondary", "tertiary" etc. are used to distinguish one element from another. Note that the words "first", "second", "third" and "fourth", "primary", "secondary", "tertiary" etc. are used here and elsewhere for labelling purposes only and are not intended to denote any specific spatial or temporal ordering.

Furthermore, the labelling of a first element does not imply the presence of a second element and vice versa.

It is to be noted that the word "comprising" does not necessarily exclude the presence of other elements or steps than those listed.

It is to be noted that the words "a" or "an" preceding an element do not exclude the presence of a plurality of such elements.

It should further be noted that any reference signs do not limit the scope of the claims, that the exemplary embodiments may be implemented at least in part by means of both hardware and software, and that several "means", "units" or "devices" may be represented by the same item of hardware.

Figure 1:
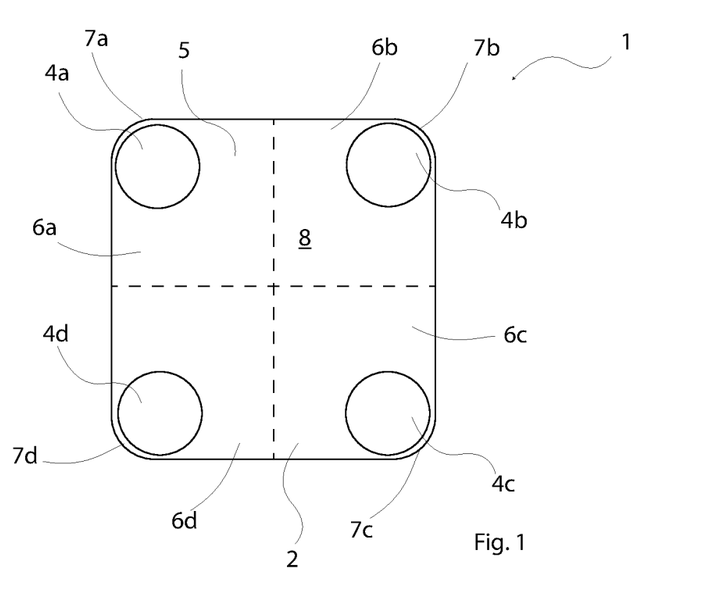
FIG. 1 is a top view of a base element in accordance with the present disclosure.
Figure 2:
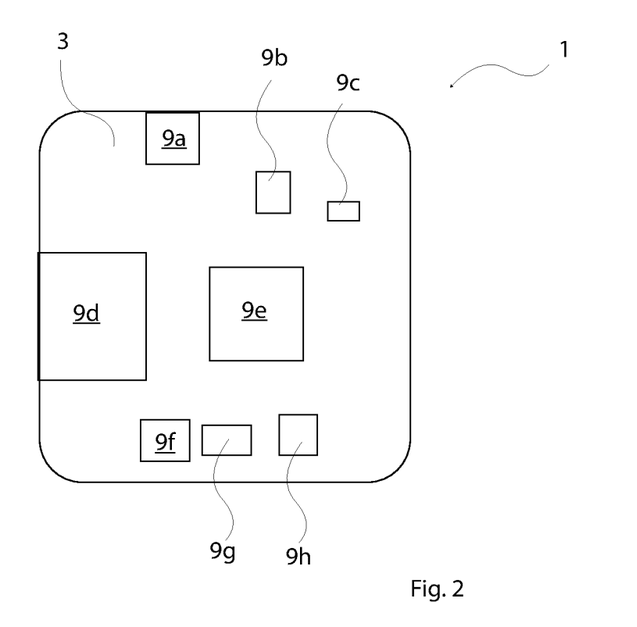
FIG. 2 is a bottom view of a base element in accordance with the present disclosure.

FIG. 1 shows a top view of a load sensing device 1 having a base element 8, where the base element comprises a first side 2, and an opposite second side 3 (shown in FIG. 2). The base element comprises a first load sensing element 4a, a second load sensing element 4b, a third load sensing element 4c and a fourth load sensing element 4d. The first side 2 has an outer surface 5, where the outer surface 5 may divided into a first area 6a, second area 6b, third area 6c and a fourth area 6d, where each of the areas 6a-6d comprises a load sensing element 4a-4c. In this example, the load sensing elements 4a-4c are positioned on the four corners 7a-7d of the base element 8, so that the load sensing elements are separated from each other, and that each load sensing element is capable of measuring the application on a force on a separate area 6a-6c of the outer surface 5 of the base element 8.

The exemplary device shown in FIG. 1-4 is a device having four load sensing elements 4a-4d, but in other applications the load sensing device 1 may have two load sensing elements, three load sensing elements, six load sensing elements, or an array of load sensing elements. If the load sensing device has a plurality of load sensing elements, it is to be understood that within the understanding of the present description at least two of the load sensing elements are separated from each other. Furthermore, in the event that two load sensing elements are overlapping, it may be possible to use signal processing to separate the signals in order to have two load sensing elements that are separated from each other. The meaning of the term separated from each other may be understood as having the possibility of measuring two different load signals from two different positions on the base element.

FIG. 2 shows a bottom view of the base element 8 of the load sensing device 1, where the base element 8 comprises a second side 3, as well as a plurality of electrical components 9a-9h. The electrical components 9a-9h may be any of a controller, memory, wireless transmitter/receiver, accelerometer, gyroscope, humidity sensor, haptic feedback device (vibrator), multiplexer, connection interface, power interface, etc. The electrical components 9a-9h may be connected to each other in accordance with their functioning, where the controller may e.g. be connected to the memory, the wireless interface, the connection interface, the load sensing elements 4a-4d which area positioned on the opposite side of the base element 8. The base element may e.g. be a print board, where the electrical components are soldered to the board, and the electrical connections between the electrical components are integrated into the print board. Furthermore, the load sensing devices 4a-4d may be connected through the base element 8 from the first side to the second side, where the electrical connections between the electrical components and the load sensing device are integrated in the print board. Alternatively, the electrical connections may be wired in accordance with known methods of providing electrical connections. Furthermore, the electrical connections between the electrical components and/or the load sensing elements may be a mixture of integrated circuits and/or wired connections.

Figure 3:
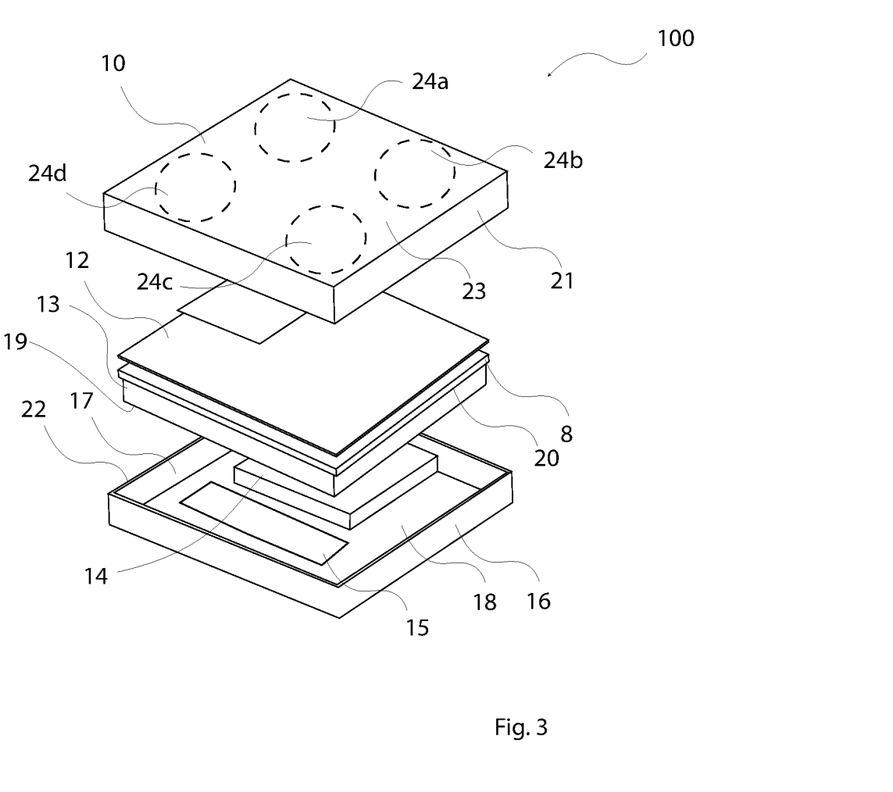
FIG. 3 is an exploded view of a load sensing device in accordance with the present disclosure.

FIG. 3 shows an exploded view of a load sensing device assembly 100, where the load sensing device assembly 100 comprises, from top to bottom, a first housing element 10, an NFC antenna 11, a foil 12, a base element 8, an insert 13, a battery 14, a charging coil 15, a second housing element 16.

The second housing element 16 comprises an inner volume 17, which is configured to house the inner components of the load sensing device 1, where in this example the first housing element 10 and the second housing element 16 provide the outer surface of the load sensing device 1 when the load sensing device 1 is in its assembled state. The second housing element may be provided with a charging coil 15, which allows for wireless charging of the battery 14 which is provided inside the inner volume 17 of the second housing element. The insert 13 may have a lower part 19 that is configured to come into direct or indirect mechanical contact with an inner surface 18 of the second housing element, while an upper part 20 of the insert 13 abuts the second side 3 of the base element 8, where the insert 13 is capable of transmitting force that is applied to the base element to the inner surface 18 of the second housing element 16. The insert 13 may also provide a stability to the base element 8. This means that the second housing element can function as a counterforce to the base element, when a load is applied to the first side of the base element.

The peripheral edge 21 of the first housing element 10 may fit into the inner volume 17 of the second housing element 16, or may extend outside the peripheral edge 22 of the second housing element 16. This means that the first housing element 10 and the second housing element 16 provide the outer surface of the load sensing device. The first housing element 10 has an upper surface 23, where the upper surface 23 may be made of a flexible material so that any force that is applied to the upper surface 23 causes the upper surface to flex in at least four flex areas 24a-24d, where the flex areas 24a-24d area positioned above the load sensing elements 4a-4d (shown in FIG. 1a) allowing the force to be transmitted to the load sensing elements 4a-4d during the application of force to the upper surface and/or the flex areas 24a-24d. Optionally, the entire upper surface 23 may be made out of a flexible material, where the flex areas 24a-24 are integral parts of the flexible upper surface.

The device 1 may be provided with an NFC antenna 11, where the NFC antenna 11 is positioned between the base element 8 and the first housing element 10. Furthermore, the foil 12 may be provided between the NFC antenna 11 and the first side 2 of the base element 3, in order to provide insulation between the NFC antenna 11 and the base element. The foil may be flexible, allowing force which is applied to the first housing element to be transferred to the load sensing elements 4a-4c of the base element 8.

Figure 4A:
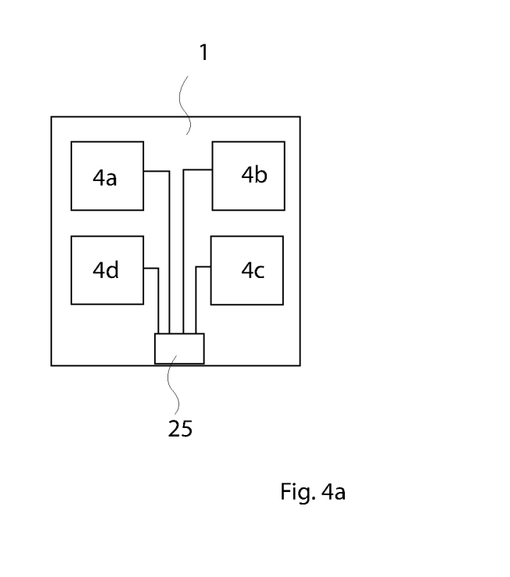
FIGS. 4a and 4b are schematic diagrams of a load sensing device in accordance with the present disclosure.

FIG. 4a shows a schematic diagram of an exemplary load sensing device where the load sensing elements 4a-4d are connected to an interface 25. The interface 25 may be part of an electrical component, such as a controller, or may be a separate entity adapted to provide a connecting interface to the electrical components.

Figure 4B:
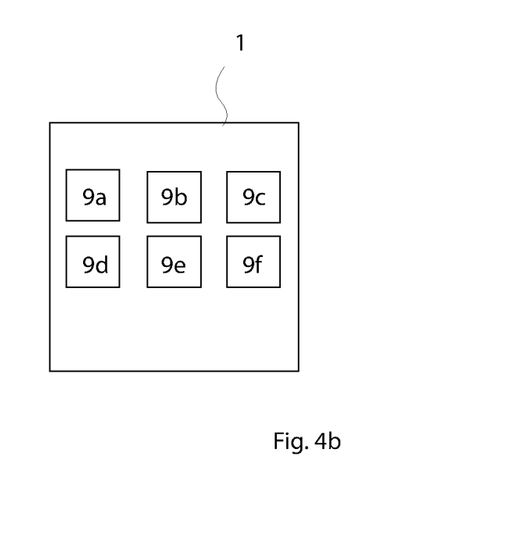

FIG. 4b shows a schematic diagram of an exemplary load sensing device 1, where the load sensing device 1 comprises a processing unit 9a, a memory 9b and an interface 9c. The processing unit 9a may be used to communicate with the load sensing devices 4a-4d shown in FIG. 4a and to receive the electrical signal from the load sensing devices 4a-4d, and optionally to store the values in the memory 9b. The interface 9c may be a wired or wireless interface, where the interface may be used to provide communication between a computer (not shown) and the load sensing device 1. The load sensing device may further comprise an accelerometer 9d, a gyroscope 9e, a humidity sensor 9f which are connected to the processing unit 9a which is capable of receiving the electrical signals from the accelerometer 9d, the gyroscope 9e and the humidity sensor 9f and store these e.g. in the memory.

Although features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications, and equivalents.

The invention claimed is:

1. A load sensing device for a shoe, the load sensing device comprising:
   a base element having a first side and an opposite second side, where the first side has a predefined area; and
   a first load sensing element and a second load sensing element positioned at the first side of the base element,
   wherein the first load sensing element is positioned in a first area of the predefined area of the first side and the second load sensing element is positioned in a second area of the predefined area of the first side,
   wherein the first load sensing element has a fixed position relative to the second load sensing element during use, the fixed position being fixed in three dimensions, and where the first load sensing element and the second load sensing element are configured to measure a load applied to at least part of the predefined area of the first side.

2. The load sensing device in accordance with claim 1, wherein the first load sensing element and/or the second load sensing element is/are configured to measure a plurality of values of loads.

3. The load sensing device in accordance with claim 1, wherein the predefined area of the first side is configured to be positioned in a heel area of the shoe.

4. The load sensing device in accordance with claim 1, wherein the first area of the predefined area of the first side is separated from the second area of the first side.

5. The load sensing device in accordance with claim 1, further comprising electrical connections providing electrical communication from the first load sensing element and the second load sensing element to electrical components.

6. The load sensing device in accordance with claim 1, further comprising a housing having at least a first side which covers at least one of: the first side of the base element, the first load sensing element, or the second load sensing element, and
wherein the first side of the housing is flexible allowing force applied to the surface of the housing to be transmitted to the first load sensing element and/or the second load sensing element.

7. The load sensing device in accordance with claim 6, wherein the housing further includes a second side which covers the second side of the base element, and/or the second side of the housing is configured to provide a counterforce to the first load sensing element and the second load sensing element during use.

8. The load sensing device in accordance with claim 1, wherein the first load sensing element and/or the second load sensing element is a force sensitive resistor.

9. The load sensing device in accordance with claim 1, wherein the base element is a rigid element.

10. The load sensing device in accordance with claim 1, wherein the base element is a printed circuit board, having electrical connections providing electrical communication from the first load sensing element and the second load sensing element on the first side of the base element to the second side of the base element.

11. The load sensing device in accordance with claim 1, wherein the second side of the base element comprises one or more electrical components.

12. The load sensing device in accordance with claim 1, further comprising a controller.

13. The load sensing device in accordance with claim 1, wherein the first side of the base element comprises at least a third load sensing element.

14. The load sensing device in accordance with claim 1, further comprising elements for measuring one or more of the following: acceleration, direction, humidity, position, orientation, temperature, barometric pressure, and/or or angular velocity.

15. A method of obtaining load measurements in an article of footwear, the load measurements originating from a sole of a foot of a user, the method comprising:
positioning a first load sensing element in a first region of an article of footwear, the first load sensing element providing a first electrical signal;
positioning a second load sensing element in a second region of an article of footwear, the second load sensing element providing a second electrical signal;
fixing the position of the first load sensing element, in three dimensions, relative to the second load sensing element during use; and
receiving the first and the second electrical signal by a processing unit during use of the article of footwear.

* * * * *